(12) United States Patent
Giniger

(10) Patent No.: US 8,377,421 B2
(45) Date of Patent: Feb. 19, 2013

(54) TOOTH GLOSSING OR FINISHING COMPOSITIONS FOR ORAL CARE

(76) Inventor: Martin S. Giniger, New York, NY (US)

( * ) Notice: Subject to any disclaimer, the term of this patent is extended or adjusted under 35 U.S.C. 154(b) by 1200 days.

(21) Appl. No.: 11/356,317

(22) Filed: Feb. 15, 2006

(65) Prior Publication Data

US 2006/0198799 A1    Sep. 7, 2006

Related U.S. Application Data

(66) Substitute for application No. 60/734,477, filed on Nov. 7, 2005.

(60) Provisional application No. 60/653,421, filed on Feb. 15, 2005, provisional application No. 60/734,549, filed on Nov. 7, 2005.

(51) Int. Cl.
| | |
|---|---|
| *A61Q 11/00* | (2006.01) |
| *A61K 8/00* | (2006.01) |
| *A61K 8/73* | (2006.01) |
| *A61K 8/92* | (2006.01) |
| *A61K 8/97* | (2006.01) |

(52) U.S. Cl. ............. 424/49; 424/58; 424/401; 536/123
(58) Field of Classification Search .................... 424/49, 424/58, 401; 536/123
See application file for complete search history.

(56) References Cited

U.S. PATENT DOCUMENTS

| | | | | |
|---|---|---|---|---|
| 4,996,044 | A | * | 2/1991 | Mercado et al. ................. 424/64 |
| 5,503,825 | A | * | 4/1996 | Lane ............................... 424/64 |
| 5,512,278 | A | * | 4/1996 | Mundschenk ............. 424/78.06 |
| 6,333,024 | B1 | * | 12/2001 | Masters et al. ................... 424/49 |
| 6,475,470 | B1 | * | 11/2002 | Kayane et al. ................... 424/49 |
| 6,586,213 | B2 | * | 7/2003 | Kobzeff et al. ............... 435/104 |
| 2002/0041788 | A1 | * | 4/2002 | Look et al. ....................... 401/68 |
| 2002/0137728 | A1 | * | 9/2002 | Montgomery .................. 514/99 |
| 2003/0039617 | A1 | * | 2/2003 | White et al. ..................... 424/49 |
| 2008/0274067 | A1 | * | 11/2008 | Chaffer et al. .................. 424/53 |

* cited by examiner

*Primary Examiner* — Lezah Roberts
(74) *Attorney, Agent, or Firm* — Peter B. Scull; Hamilton, DeSanctis & Cha, LLP

(57) ABSTRACT

A tooth glossing and/or finishing composition including one or both of a wax and an acidic neutralizer with an optional additive of a vegetable gelling agent.

14 Claims, No Drawings

TOOTH GLOSSING OR FINISHING COMPOSITIONS FOR ORAL CARE

CROSS-REFERENCE TO RELATED APPLICATIONS

The present invention claims the benefit of and priority from the prior-filed U.S. Provisional Patent Applications, No. 60/653,421; filed Feb. 15, 2005, entitled "Whitening System Capable of Delivering Effective Whitening Action"; and No. 60/734,549; filed Nov. 7, 2005, entitled "Oral Care Compositions and Methods"; and No. 60/734,477 filed Nov. 7, 2005, entitled "Compositions for Enhancing the Effects of Other Oral Care Compositions"; the subject matter of each of which hereby being specifically incorporated herein by reference for all that they disclose and teach.

BACKGROUND

The present invention relates to improvements in oral care compositions, and in some primary implementations, more particularly relates to either a standalone tooth glossing or a finishing composition for oral care.

In the state of the art of oral care compositions and the delivery of such compositions to the site of use in the oral cavity, many means and methods have been utilized and yet numerous issues remain. For an effective ingredient of an oral care composition to have a beneficial or therapeutic effect, whether for oral cleaning, treatment, or tooth whitening, the effective ingredient must reach and preferably maintain effective contact with the oral care feature long enough to provide its intended effect. Moreover, a variety of oral care procedures, though effective in their own right, can leave other perhaps undesirable side effects, particularly, after completion of their intended uses. The present invention is directed to either or both or other desirable oral care effects.

SUMMARY

Tooth glossing and/or finishing compositions are described here. For stand-alone tooth glossing, a principal ingredient is a wax with an optional vegetable gel component. An acidic component may be used for a finishing composition particularly in an alkaline tooth cleaning environment, as for example used for solvent and surfactant cleaning with alkaline components, or an alkaline environment which may be used for activating peroxide whiteners and/or accelerating the formation of free radicals from the peroxide to effect the oxidation of organic molecules causing staining of the dentition. Such a finishing composition hereof may thus be used for post application to the dentition after the application of any alkaline cleaning or whitening compositions.

The primary components of many compositions hereof may be in a liquid or a substantially solid form. If in liquid form, the solvent may be water, or the like, with an emulsifier to aid in obtaining a solution for the wax. If in substantially solid form, a solvent may, though may more typically, may not be used, a wax serving as the base. In many implementations, a wax such as carnuba, candellila beeswax or a microcrystalline wax or the like may be used. Exemplary acids that may be used include citric acid or tartaric acid to form an acidic composition. Other acidic compounds may alternatively be used. Other additives for taste, texture, viscosity, and other oral care or oral hygiene purposes may also be included in the composition hereof.

The tooth glossing composition may be used as part of a tooth whitening process to enhance the effect of a whitening composition. In addition, a finishing composition hereof may be used after the application of the whitening composition to neutralize the alkaline environment in the oral cavity caused by alkaline whitener compositions or cleaners, or by an alkaline whitening or cleaning process and thereby return the user's mouth to a neutral pH.

DETAILED DESCRIPTION

The detailed description set forth herein is intended as a description of several exemplary oral care compositions. These may be used for enhancing tooth whitening and/or other oral care processes or compositions; however, this is not intended to represent the only forms in which such compositions may be prepared or utilized. The description sets forth features of and steps for preparing and using the present compositions; however, it is to be understood that the same or equivalent ingredients incorporated in different embodiments of oral care compositions may accomplish the same functions or achieve the same results and such compositions are also intended to be encompassed within the spirit and scope of this description.

The present invention is directed primarily to tooth glossing compositions which may be used as part of a tooth whitening process to enhance the effect of a whitening composition, and/or to finishing compositions which may be used after the application of the whitening composition to neutralize the alkaline environment in the oral cavity caused by alkaline whitener compositions or cleaners, or by an alkaline whitening or cleaning process and thereby return the user's mouth to a neutral pH. Thus, tooth glossing and/or finishing compositions are the primary compositions hereof.

For both embodiments, a principal ingredient may be a wax, typically with an optional vegetable gel component (e.g., Vegelatum or Vegelatum Clear RM, available from NutriBios Corporation, Ontario, Canada) included. As such, a tooth glossing composition may be formed. Tooth glossing can be used to enhance the visual appeal of the teeth by making them appear brighter and/or more lustrous. This may be beneficial for its own sake, or may be used in conjunction with other processes or compositions the enhance the effectiveness or apparent effectiveness thereof. For example, tooth whitening processes and compositions have as their primary goal the achievement of brighter and/or whiter looking teeth. A tooth gloss such as is described here can enhance the brightness of the teeth and thereby enhance the overall whitening of teeth.

In a primary implementation, a tooth gloss hereof may be of and/or include a wax. Waxes such as carnuba, candellila beeswax or a microcrystalline wax or other orally acceptable waxes may be exemplar waxes to be used herefor. Other waxes may be substituted. In a primary form, the wax can exist as a solid or substantially as a solid as waxes would under normal operating conditions. Such a wax could then be applied from the solid or substantially or semi-solid form directly to the tooth for the purposes hereof. Alternatively, the wax may be in a carrier of water and/or oil, and appear as a solid, semi-solid or fluid or liquid. Or, the wax may be in or may be made a substituent of a fluid form. In some cases, this would involve dissolving the wax into a solvent such as water; however, typically, an emulsifier may be used to aid in obtaining a solution for the wax. Note, a solvent could also be used even with a wax in substantially solid form, though more typically, this would be less often the case, the wax instead serving as the base. In any case, the composition may appear as a paste, gel or liquid or in another format, not listed.

As introduced above, an optional vegetable gel component, such as the Vegelatum or Vegelatum Clear RM products, may be included to the wax compound. An enhanced tooth glossing composition may be created hereby. A vegetable gelling component may be made from one or more of many types of vegetable oils, such as canola oil, and may be thickened by a vegetable product such as celery or a derivative from celery. A gelling product not unlike a petroleum gelling product may thus be formed, however, without any petroleum or like product which would generally not be orally acceptable. Other ingredients may be added as described below.

An acidic component may be used as well for a finishing composition particularly for use in or with an alkaline tooth cleaning environment, as for example used for solvent and surfactant cleaning with alkaline components, or an alkaline environment which may be used for activating peroxide whiteners and/or accelerating the formation of free radicals from the peroxide to effect the oxidation of organic molecules causing staining of the dentition. Such a finishing composition hereof may thus be used for post application to the dentition after the application of any alkaline cleaning or whitening compositions.

With the acidic composition, the primary components of many compositions hereof may here as well be in a liquid or a substantially solid form as described above. If in liquid form, the solvent may be water, or the like, however, if in substantially solid form, the wax may serve as the base. Thus, an acidic or other finishing composition may be an acid in a carrier such as water and/or wax, in liquid and/or solid or semi-solid form. In many implementations, exemplary acids that may be used include citric acid or tartaric acid to form an acidic composition. Other acidic compounds may alternatively be used.

An alkaline environment may have been created either for cleaning, e.g., when using a solvent surfactant and alkaline composition such as is described in co-pending patent application Ser. No. 11/356,316, entitled STAND-ALONE OR ENHANCER COMPOSITION FOR ORAL CARE, filed Feb. 15, 2006, which is hereby incorporated herein by reference, or for activating peroxide or other whiteners to thereby accelerate the formation of free radicals from the peroxide to effect the oxidation of organic molecules causing staining of the dentition. In some cases, an enhancing composition may be provided as described in the co-pending application Ser. No. 11/356,445, entitled COMPOSITIONS FOR ENHANCING EFFECTS OF OTHER ORAL CARE COMPOSITIONS, filed Feb. 15, 2006, which is hereby incorporated herein by reference, for advance application to the dentition before the application of any whitening compound. The primary active component of such an enhancing composition may be a base compound such as potassium hydroxide (KOH), though other basic compounds may alternatively be used to create the alkalinity of the enhancing composition. An acidic finishing composition hereof can thus counteract the alkaline state of the oral features having been treated and return them and/or the entire oral cavity to a more desirable neutral pH.

Other additives for texture, viscosity, taste, and other oral care or oral hygiene purposes may also be included in the composition hereof.

Compositions according to the present invention may further include a surfactant. Typically, this would be of about 1% to about 2% of the overall composition. Suitable surfactants may be anionic, nonionic, amphoteric, zwitterionic, cationic, and mixtures thereof. Anionic surfactants include, but are not limited to water-soluble salts of alkyl sulfates having from 8 to 20 carbon atoms in the alkyl radical (e.g., sodium alkyl sulfate), water-soluble salts of sulfonated monoglycerides of fatty acids having from 8 to 20 carbon atoms, and mixtures thereof. Examples of anionic surfactants include sodium lauryl sulfate, sodium coconut monoglyceride sulfonates, phospholipids, sarcosinates such as sodium lauryl sarcosinate, taurates, sodium lauryl sulfoacetate, sodium lauroyl isethionate, sodium laureth carboxylate, and sodium dodecyl benzenesulfonate. Many of these anionic surfactants are disclosed in U.S. Pat. No. 3,959,458, which is hereby incorporated herein by reference in its entirety.

Other alternatively added texture agents may include xanthan gum or a clear xanthan gum. Such a gum may act as a stabilizer, thickener and/or suspending agent; available from Jungbunzlauer AG, Basel, Switzerland.

An antioxidant may be included, particularly for use after an oxidizing whitening treatment to scavenge free radicals. An antioxidant of a pomegranate, apple, pineapple or other fruit extract may be used. Such fruit extracts may act as flavorants as well.

The composition hereof may further include ingredients for affecting the taste and feel of the enhancing composition by a user. For example, flavorants such as methyl salicylate, thymol, menthol, eucalyptol (Listerine) or flavor oils such as peppermint oil or cinnamon oil may be included to provide a pleasing flavor to the enhancing composition. Sodium saccharin, sucralose, aspartame, or other sweetening agents may be used to enhance the flavor. Sodium citrate may be added as an anticoagulant to improve the feel of the enhancing composition in the mouth. It may also enhance the effectiveness of any surfactant by preventing interference from any calcium ions present. Moreover, a composition hereof, particularly in liquid format, may further include witch hazel or the like (up to about 11%). This would enhance the composition as a mouth rinse.

In practice, it may in some embodiments be preferred to include an acidic component, to adjust the pH of the overall composition. The pH of the composition is from, for example, about 5 to about 8, or for a further example, from about 5.5 to about 6.5. Exemplar acidic components include citric and/or tartaric acids, typically up to about 1%.

Note also, fluoride or fluoride-containing compounds may be included herein also to be used in fluoridating teeth. Thus, when applied either onto or into dental tissue, particularly in the presence of fluoride, the compositions hereof may operate to promote fluoridation. Such fluoridation or other mineralization may serve to assist in prevention and/or repair of dental weaknesses such as dental caries, exposed roots and dentin sensitivity.

The compositions hereof can also include other active ingredients, such as de-sensitizing agents and/or antimicrobial or antibacterial agents. Even with improved efficiency and shorter treatment times, some patients may still experience sensitivity from tooth whitening compositions. Inclusion of desensitizing agents in the enhancing composition allows time for desensitization of the oral tissue after the application of the whitening compound. Suitable desensitizing agents can include Eugenol and/or alkali nitrates such as potassium nitrate, sodium nitrate, and lithium nitrate and other potassium salts such as potassium chloride and potassium bicarbonate. The desensitizing agent may make up to about 3% to 5% percent by weight of the composition. Eugenol may also act as an antimicrobial or antibacterial agent.

A composition hereof may further include a tartar control agent such as one or more of triclosan and sodium pyrophosphate. Furthermore, a composition hereof may further include an anti-gingivitis agent such as one or more of cetyl pyridinium chloride and triclosan.

Further additives may include calcium nitrate and/or sodium mono and/or dibasic hydrate. These compounds may be added to lower the viscosity of the enhancing composition and provide a composition that has greater ability to penetrate recesses and interstices of the dentition. Such additives may also improve the stability of the enhancing composition. Potassium nitrate may alternatively and/or additionally be added to achieve desired viscosity effects.

In addition, optional additives including emulsifiers, flavorings, colorants, coloring agents, anti-plaque agents, anti-staining compounds, excipients such as emollients, preservatives, other types of stabilizers such as antioxidants, chelating agents, tonicity modifiers (e.g., sodium chloride, manitol, sorbitol, or glucose), spreading agents, pH adjusting agents and water soluble lubricants, e.g., propylene glycol, glycerol, or polyethylene glycol may be included in the enhancing composition. The concentration of each may easily be determined by a person skilled in the art. Lecithin, a natural emulsifier found in soy and other plants, and gum arabic, which comes from the sap of certain species of acacia trees, can be added for use as an emulsifier, dispersant, and/or wetting agent. Suitable preservatives may include benzalkonium chloride, parabens, chlorhexidine acetate, chlorhexidine gluconate, sorbic acid, potassium sorbitol, chlorbutanol, and phenoxyethanol. Suitable emollients such as those used for topical applications are, for example, di-n-octyl ether, fatty alcohol polyalkylene glycol ether, 2-ethylhexyl palmitate, and isopropyl fatty acid esters.

Composition according hereto may further include cleaning agents such as solvents and/or abrasives. Thus, included may be one or both of an alcohol cleaning solvent and a baking soda cleaning abrasive, among other alternative cleaning additives.

The compositions hereof may be applied to a user's dentition in any of a variety of ways. For example, if the composition has a low viscosity, the enhancing composition may be provided in the form of liquid such as a mouth rinse. At a higher viscosity, for example, in the form of a gel or paste or solid or semi-solid wax, the composition may be applied with a brush or a swab, or may simply be applied by finger or straight from a container, in one example, like a lip stick or lip glossing agent. The composition may be in the form of a tooth paste and applied with a tooth brush. The composition may also be applied with a brush more closely resembling a paint brush. If the composition is applied with a swab, particularly if the composition is either a liquid or a gel, the swab may be formed of an absorptive foam material rather than other materials. Foam is more structurally sound and uniformly absorptive as compared to cotton swabs or other materials. Foam also may also be more resistant to breaking down and may not permanently deform.

As introduced, the composition hereof may be a tooth gloss, or a finishing composition, or in addition to the tooth glossing composition, the composition may also be a finishing composition. In either case, a post-whitening composition hereof may also be used as part of a complete tooth whitening process. The primary purpose of the post-whitening composition would be to return the pH within the user's mouth after a bleaching application to neutral. An exemplary bleaching composition is described in copending U.S. patent application Ser. No. 11/356,468, entitled "Oral care compositions and methods," filed Feb. 15, 2006, which is hereby incorporated herein by reference. Any other commercially available bleaching or whitening composition may likewise be used in conjunction with the compositions hereof. Some finishing compositions hereof maybe slightly acidic, for example, about 5.5 pH, to reduce the pH from the more basic level of between 8.5 and 9.5 created by the enhancing composition to neutral pH of about 7.

In a process of use of an acidic finishing composition hereof, first, an alkaline whitening or cleaning composition may be applied. Then, according to the description herein the composition hereof may be applied to a user's dentition. As indicated above, application of the enhancing composition may be by rinse, swab, or brush. This would then provide a neutral pH to the worksite. A further process may be involve wherein a preliminary enhancing composition for creating an alkaline environment may also be used such as that described in co-pending application Ser. No. 11/356,445, entitled COMPOSITIONS FOR ENHANCING EFFECTS OF OTHER ORAL CARE COMPOSITIONS, which is incorporated herein by reference. Then, once the enhancing is done, or simultaneously therewith, a whitening composition may be applied to the user's dentition. As before, the whitener or bleaching or alkaline cleaning agent may be any of a myriad of available products available over-the-counter or for clinical application, e.g., gels and pastes for brush-on or tray application and adhesive strips. Then after the whitening or cleaning process, finally, an acidic finishing composition according to the description herein may be applied to the user's dentition. The finishing composition operates to neutralize the basic pH environment created in the user's mouth by the enhancing composition or the whitening or cleaning process or components to increase the effectiveness of the whitening or cleaning process. The finishing composition may be applied over a period of about a second or a few seconds up to approximately a few minutes, or left on without time limit to ensure effective neutralization.

It may first be noted that either of these compositions, i.e., a pre-whitening composition and/or a post-whitening composition, may be used, manufactured and/or sold completely separately one from another, and indeed may be distributed apart from the whitening composition(s). In some instances, a user may use only a pre-whitening composition and then a whitening composition with or without a post-whitening composition; and in other instances, a user may use a whitening agent and a post-whitening composition without a pre-whitening composition. Even so, it may be preferred to use all three in order; namely, a pre-whitening composition, then, a whitening agent or agents (see below), and finally a post-whitening composition as described hereinabove. In such a case, the combination may be referred to as a three-component system (pre-whitening, whitening, and post-whitening). In some other instances, the whitening composition/system itself may occur in one or two or more components as described in the co-pending patent application Ser. No. 11/355,925, FOAMING COMPOSITIONS AND METHODS, filed Feb. 15, 2006, and the overall system may then reflect the total number of components. For example, when the whitening system itself includes two components, then, a system hereof may be a four-component system; namely, a pre-whitening component, whitening in two component parts, and a post-whitening component. The method of use hereof would be with the modification of including the mixing of the two parts of the whitening composition prior to or during application thereof to the dental surfaces, after the initial pre-whitening enhancing application and before the post-whitening application.

The above specification, examples and data provide a complete description of the structure, process, and use of exemplary embodiments of the invention. Although various embodiments of this invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A composition for oral use as one of a tooth gloss or a finishing composition to enhance the appearance of the dentition, the composition comprising a wax as a base for the composition, a vegetable gelling agent, clear xanthan gum, witch hazel, an antioxidant, one or both of a neutralizer and pH adjuster to create an acidic composition, and a preservative; wherein the composition is a solid, solventless wax-based form for direct application to a tooth.

2. A composition according to claim 1 further including an emulsifier.

3. A composition according to claim 1 further including a surfactant.

4. A composition according to claim 1 further including one or both of a neutralizer and pH adjuster which is one or more of citric acid or tartaric acid.

5. A composition according to claim 1 further including a tartar control agent.

6. A composition according to claim 1 further including an anti-gingivitis agent.

7. A composition according to claim 1 further including a fluoride.

8. A composition according to claim 1 further including a preservative.

9. A composition according to claim 1 further including one or more of a flavorant or colorant.

10. A composition according to claim 1 further including one or both of an alcohol cleaning solvent and a baking soda cleaning abrasive.

11. A composition according to claim 3, wherein the surfactant is 1% to about 2% of the overall composition.

12. A composition according to claim 1, wherein the witch hazel is up to about 11% of the overall composition.

13. A composition according to claim 1, wherein the pH of the composition is between 5.5 and 6.5.

14. A composition according to claim 4, wherein the citric acid or tartaric acids is up to 1% of the overall composition.

* * * * *